(12) United States Patent
Buttry et al.

(10) Patent No.: US 6,473,171 B1
(45) Date of Patent: Oct. 29, 2002

(54) BIOCOMPATIBLE APPARATUS FOR ULTRASENSITIVE AND RAPID DETECTION OF CONTAMINANTS IN LIQUIDS

(75) Inventors: Daniel A. Buttry; Guoying Chen, both of Laramie, WY (US)

(73) Assignee: Coors Brewing Company, Golden, CO (US)

( * ) Notice: Subject to any disclaimer, the term of this patent is extended or adjusted under 35 U.S.C. 154(b) by 0 days.

(21) Appl. No.: 09/456,538

(22) Filed: Dec. 8, 1999

Related U.S. Application Data
(60) Provisional application No. 60/116,164, filed on Jan. 15, 1999.

(51) Int. Cl.[7] .............................................. G01N 21/05
(52) U.S. Cl. ........................................ 356/246; 356/73
(58) Field of Search ............................. 356/72, 73, 246

(56) References Cited

U.S. PATENT DOCUMENTS

| | | | |
|---|---|---|---|
| 3,871,770 A | 3/1975 | von Behrens et al. ...... 356/103 |
| 4,110,604 A | 8/1978 | Haynes et al. | |
| 4,165,484 A | 8/1979 | Haynes | |
| 4,343,551 A | 8/1982 | Eisert ......................... 356/335 |
| 4,348,107 A | 9/1982 | Leif | |
| 4,660,971 A | 4/1987 | Sage et al. ..................... 356/39 |
| 4,661,913 A | 4/1987 | Wu et al. | |
| 4,662,742 A | 5/1987 | Chupp ......................... 356/39 |
| 4,786,165 A | 11/1988 | Yamamoto et al. | |
| 4,818,103 A | 4/1989 | Ihomas et al. ................. 356/72 |
| 4,983,038 A | 1/1991 | Ohki et al. .................. 356/246 |
| 4,988,619 A | 1/1991 | Pinkel ......................... 435/30 |
| 5,007,732 A | 4/1991 | Ohki et al. .................... 356/73 |
| 5,135,302 A | 8/1992 | Hirako | |
| 5,138,181 A | * 8/1992 | Lefevre et al. ................ 356/73 |
| 5,328,954 A | * 7/1994 | Sarangapani ................ 524/589 |
| 5,547,849 A | 8/1996 | Baer et al. .................. 435/7.24 |
| 5,739,902 A | 4/1998 | Gjelsnes et al. .............. 356/73 |
| 5,783,399 A | 7/1998 | Childs et al. ................ 435/7.2 |
| 5,794,823 A | * 8/1998 | Roundtree ............... 222/400.7 |
| 5,895,764 A | 4/1999 | Sklar et al. ................... 436/63 |
| 5,980,481 A | * 11/1999 | Gorsuch ...................... 604/28 |

* cited by examiner

Primary Examiner—Richard A. Rosenberger
(74) Attorney, Agent, or Firm—Dorsey & Whitney, LLP

(57) ABSTRACT

A biocompatible flow cytometry system such that low levels of bacteria or other particles in a sample will not adsorb onto the system's surfaces. The biocompatible flow cytometry system comprises an upper chamber assembly. The upper chamber comprises a biocompatible input system, a means for retaining and adjusting the biocompatible system, a sheath fluid input port, and a means of interfacing with a glass tube. The interface between the biocompatible system and a glass tube allows for the low level contaminants to be irradiated with a laser source selected to interact with marked bacteria and cause them to fluoresce at a wavelength that can be detected.

23 Claims, 14 Drawing Sheets

VIEW B
DETAIL OF SQUARE BORE GLASS TUBE SHOWING FLUID FLOW

BIOCOMPATIBLE APPARATUS FOR ULTRASENSITIVE AND RAPID DETECTION OF CONTAMINANTS IN LIQUIDS

This application claims the benefit of U.S. Provisional Application No. 60/116,164, filed on Jan. 15, 1999.

FIELD OF THE INVENTION

The present invention relates generally to an apparatus and method for rapid and sensitive detection of contaminants in liquids, and more particularly to a biocompatible apparatus and method for detecting and measuring low levels of bacteria.

BACKGROUND OF THE INVENTION

There are many industries in which it is necessary to detect various contaminants in liquids and liquid streams. For instance, in the course of beverage processing, the beverage may become contaminated with bacteria. Once contaminated, food poisoning or spoilage often occurs. Moreover, pathogenic organisms may exist in the product and cause harm to consumers after they use or consume the product. Thus, the ability to monitor and detect the level of contaminants in liquids is critical for maintaining a product that can be consumed and/or used by humans.

As another example, it is necessary to monitor and detect the level of bacteria in the production process for beer. More specifically, undue levels of bacteria in beer, typically *Pectinatus cerevisiiphilus*, can lead to spoilage and the like where pasteurization is not utilized in the production process. The system of detection needs to be rapid and sensitive while being cost-effective. Additionally, such a detection system should desirably be automated or semi-automated so as not to be unduly labor intensive, and be configured for connection to process control systems.

Unfortunately, prior art methods for detecting bacteria contamination are too cumbersome and time consuming for immediate use. Currently, it is believed that culturing methods are being utilized. Such methods are extremely slow (requiring up to several days or so) and are very labor intensive.

One type of detection method captures the bacteria being detected on a filter medium. Detection is then achieved with chemiluminescence and fluorescence imaging. While detection can be carried out in about one hour or so and the detection-sensitivity is approximately one bacterial event in the sample, this system has no mechanism to achieve selectivity, is highly labor intensive and relatively expensive.

Further, it has been proposed to utilize immunoabsorbents and electrochemistry so as to achieve immunochemical detection. Such a system is not believed to be either automated or have suitable detection sensitivity.

It has also been proposed to employ DNA-hybridization and/or polymerase chain reaction (PCR) methods. Such methods are highly labor intensive and very dependent upon the skill of the operator.

Additionally, there has been considerable attention directed to the general area of flow cytometers and particle analysis using sheath flow chambers with laser excitation and detection of fluorescence using photodetectors. The purpose of such sheath flow chambers is to entrain the sample solution in a fast moving stream of pure water or buffer such that the sample solution is swept out of the sheath flow chamber and down into a square bore capillary. U.S. Pat. Nos. 3,871,770 and 4,343,551 disclose sheath flow chamber designs.

Many flow cytometers impinge the sample into a flat glass sheet, by way of, for example, a microscope cover slip. This forces the cells in the flow stream to experience a shear field. For mammalian cells, which are oblate spheroids, this causes such cells to align in the shear field with their short axis along the surface normal of the cover slip (see, for example, U.S. Pat. No. 4,988,619). A laser beam then impinges along the surface normal, which maximizes the scattering signal that is used to trigger the fluorescence detection channels. However, this system causes a very large amount of scattering that contributes significantly to the background signal.

U.S. Pat. No. 4,983,038 discloses one design using flow cytometry. U.S. Pat. No. 4,660,971 discloses one approach for stabilizing the optical arrangement of a sheath flow and collection system.

Another drawback with these and other flow cytometer designs is that they use glass or stainless steel components, which can adsorb bacteria, organisms or other contaminants that are to be detected. When detecting high levels of bacteria, organisms or other contaminants, this is not a serious issue. However, when attempting to detect low levels of bacteria, organisms or other contaminants, the loss of a few organisms to adsorption on the walls of the delivery tubing or other components can lead to the drastic reduction in sensitivity.

The problem with measuring low bacteria levels, for instance, is that bacteria adsorb tenaciously to many, if not most surfaces. The adsorption is accomplished in several ways: through electrostatic interactions (e.g., negatively charged bacteria adsorb to a positively charged surface) and/or hydrophobic interactions. Many bacteria also exude complex polysaccharides called exopolysaccharides (EPS). These are large hydrophobic polymeric molecules that are strongly adsorbed to many surfaces, and thereby provide an anchor point for bacteria. Several EPS types are known; some are charged. Positively charged EPS allows negatively charged bacteria to adsorb to positively charged surfaces by providing an electrostatic buffer (e.g., positive EPS adsorbs to negative surface, then negative bacterium adsorb to the positively charged EPS surface).

The tendency for bacterial adsorption at surfaces makes the detection of small numbers of bacteria difficult, primarily due to the inefficient delivery of the bacteria to the detection region. It is generally assumed that if the bacteria are actually delivered to the detection region, then they will probably be detected with little difficulty. However, as explained above, this is not the case with conventional cytometers. Rather, conventional cytometer designs using glass and/or stainless steel components are not compatible with the measurement of low levels of bacteria.

In addition, conventional flow cytometers run at very high sheath flow rates. The high sheath flow rate translates into the bacteria passing through the detection site at a very rapid rate, thus the bacteria spend a short time in the laser beam. Consequently, there are very few fluorescent photons produced for detection. For mammalian cells (which are 10,000× larger in volume than typical bacteria cells) this is not a serious issue, because their larger size means their surfaces can accommodate more label. Since there is more label present on the surfaces of the mammalian cells, the sample can run faster while still allowing for the collection of a sufficient number of fluorescent photons to detect them efficiently. However, for the much smaller bacterial cells, the high flow rates are not compatible for measuring fluorescence from such cells.

In summary, despite the considerable prior efforts in this field, there remains the need for a versatile, rapid and sensitive, cost-effective, biocompatible detection system for small levels of bacteria, organisms and other contaminants or moieties of interest.

SUMMARY OF THE INVENTION

Accordingly, the present invention provides a rapid and sensitive detection system that is capable of automation. Moreover, the invention can be utilized in a cost-effective fashion to detect a variety of contaminants in many liquid streams, as well as allowing the detection of other moieties of interest by utilizing a liquid stream.

The present invention provides a biocompatible flow cytometry system such that the bacteria or other particles in the sample will not adsorb onto the system's surfaces. This is accomplished by fitting the system with biocompatible material.

The present invention provides a system characterized by ready and easy alignment of the laser source with the sample stream. In addition, the invention provides a system capable of maximizing the signal emitting from the contaminant or other moiety being detected while minimizing the background signal, i.e., providing a system having a desirable signal/noise ratio. A principal embodiment of the invention is a system in which the detection signal is within the red region of the light spectrum.

The present invention provides a system that utilizes a flow chamber system that essentially eliminates background scattering, includes a holder which is sufficiently mechanically rugged so as to accommodate a relatively frail, thin wall square bore capillary and allows facile removal and replacement of such capillary with minimal realignment of the optical components of the system.

This description will be principally directed to the rapid detection of beer spoilage bacteria. However, it is readily appreciated by one of ordinary skill in the art that the method and apparatus described and illustrated can be employed to detect contaminants of other bacteria, and microorganisms. This system is particularly useful for detecting a particulate material of interest, preferably capable of holding at least 100 or so fluorophores. A wide variety of liquids and liquid streams in the fermentation, food and dairy industries (e.g., beverages and juices) require such detection and/or monitoring; and the present invention can be utilized for such applications.

Even further, while the more usual applications for the invention will involve the detection and/or monitoring of bacteria or the like already present in a liquid or liquid stream (e.g., beer), it should be appreciated that the invention can also be utilized in applications where it is necessary to first provide the liquid so as to capture any contaminant to be detected, for example, any technique where a vessel or environment is used for chemical or biochemical synthesis that needs to be monitored to insure the absence, or relative absence, of unwanted contaminants that would in some way hinder the synthesis. In addition, the system of this invention may be utilized to detect the level of any moiety of interest. For example, soil samples could be added to water or the like; and a moiety of interest could be detected. Additionally, this method could be used to detect the level of $E.\ coli$ in meat or the like.

Other features and advantages of the present invention will become apparent from the following detailed description and drawings. It should be understood, however, that the detailed description and specific examples, while indicating preferred embodiments of the invention, are given by way of illustration only, since various changes and modifications within the spirit and scope of the invention will become apparent to those skilled in the art from this detailed description.

DETAILED DESCRIPTION OF THE INVENTION

Figure 1:
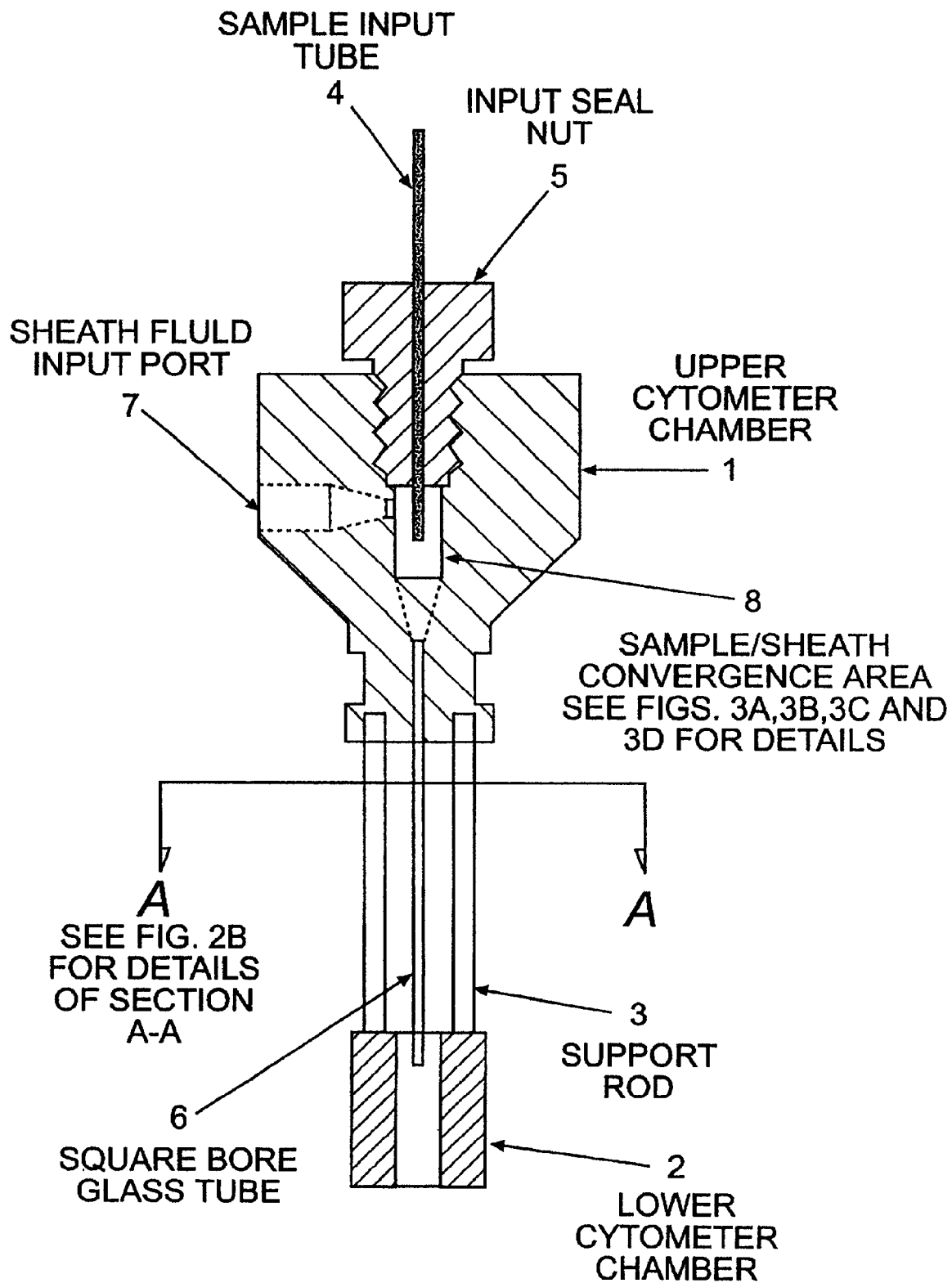
FIG. 1 illustrates one preferred embodiment of the cytometer chamber assembly.

The present invention utilizes a flow cytometer system having multiple features which includes the methodology used in the construction of the sample flow chamber, that can be combined, as required, to provide the monitoring/detection performance characteristics necessary for a particular application. In this fashion, a monitoring/detection system can be provided that is rapid, sensitive and cost-effective, achieving the performance necessary for the particular application.

The first step is to label the bacteria, contaminant or other material of interest in the sample to be analyzed. The sample is prepared so that it can be detected in such a fashion that each unit is detected. Preferably, a fluorescent label is utilized. By way of illustration, the sample size can range from a few microliters to several milliliters, depending on the measurement method used.

Labeling can be achieved by any means desired, many of which are known. As an illustrative example, affinity-based fluorescent labels can be employed, such as fluorescent-labeled antibodies, fluorescent-labeled DNA, fluorescent-labeled RNA, cell surface binding probes, or other types of fluorescent compounds to tag the organism with a fluorescent label. As is also known, such labels may be attached to the bacteria or other contaminant by direct labeling or by indirect attachment, such as by sandwich labeling.

As may be appreciated, light is directed at the fluorescent labels causing a scattering of light. Preferably, red light is directed at the sample. Accordingly, there will be excitation in the red region of the spectrum. Generally, many samples have strong background emission when excited in the blue or green regions of the spectrum. However, with red excitation the emission tends to be more red. Thus, in the preferred embodiment, the labels should provide fluorescent signals in the red region of the spectrum.

The incubation (or sample preparation step) to label any contaminants present in the sample can be carried out in any vessel desired. Illustrative suitable sample preparation times may range from about 10, or 20 to 30 minutes or so.

The incubated sample can then be analyzed by introduction into the cytometer chamber assembly shown in FIG. 1 via the sample input tube as will be discussed hereinafter. The introduction may take the form of a simple injection by a syringe.

Then, in accordance with one preferred feature of this invention, a protocol is employed to maximize the preferred fluorescence signal from the labeled bacteria while minimizing the background signals from which the desired fluorescence signal must be distinguished. Under optimum conditions, signal-to-noise ratios in excess of 100:1 can be achieved, although acceptable results can be achieved with S/N ratios as low as about 10:1.

A number of features contribute to achieving such optimum conditions. According to one preferred feature, the optimized optical system provides a path from the detection region to the detector designed to keep scattering from the square bore capillary walls from impinging on the detector. Such scattering is generated from the place where the laser beam initially strikes the glass as it enters the square bore, as well as from the area where the beam exits the square bore.

Another feature utilizes optics that select the wavelengths that impinge on the detector. Filters are employed that reject the laser wavelength while passing wavelengths in a preselected region. In this fashion, the wavelength of the fluorescence signal passes to the detector while rejecting all, or substantially all, of the other wavelengths, such as what might be observed from fluorescence of the square bore capillary, Raman scattering from the water or other components of the sheath or sample fluids in the irradiated region, and other sources of background signals.

Yet another preferred feature utilizes sufficiently slow sheath fluid velocities so as to maximize the number of fluorescent photons that can be captured while the sample fluid passes through the detection region. To this end, sheath flow velocities are generally in the range of from about 1 to about 75 cm/second. Preferably, the sheath flow velocities range from about 20 to about 40 cm/second.

A still further preferred feature employs a fluorescence detection system that continuously examines the sample region. Similarly, the detection system accumulates the pulses (i.e., which correspond to the passage of a labeled bacterium) continuously.

Another feature of the most preferred embodiment of the present invention utilizes laser excitation which is in the red region of the spectrum. More particularly, this minimizes the effects of background fluorescence since many samples of interest, particularly in the food area, for example, do not fluoresce in the red region of the spectrum. From the hardware standpoint, utilizing the red region allows use of a solid state laser. Such lasers have the characteristics of relatively low power consumption, small size and ease of use.

The flow cytometer system may comprise an upper cytometer chamber in which the sample is injected through a sample input tube and a sheath fluid input port through which the sheath fluid is introduced to entrain the sample solution and carry it into, and through, a glass tube, during which the monitoring/detection takes place, a lower cytometer chamber into which the sheath fluid and sample fluid enter after the monitoring/detection takes place, means such as support rods for attaching the upper and lower cytometer chambers together, and an optical system for carrying out the monitoring/detection functions. This optical system includes an energy source, preferably a laser, to excite the labeled bacteria and appropriate optics to detect such labeled bacteria.

The sample input system (or tube) is plays an important role in the success of the invention. In part, the most preferred embodiment of this invention utilizes highly biocompatible and chemically resistant tubing to deliver the sample to a biocompatible injection loop and associated injection valve, followed by an additional length of tubing that is connected at one end to the valve and the other end of which ultimately passes through an input seal nut and into the sample/sheath flow chamber. Preferably, the sample is injected to the biocompatible injection loop via a syringe. The use of biocompatible and chemically resistant tubing allows keeping the sample delivery system clean so as to prevent irreversible bacterial adhesion to the tubing. Such adhesion can be eliminated by rinsing the tubing with aggressive solvents, such as isopropanol/water mixtures, and also by rinsing with water/surfactant solutions.

The injection valve is set so that the sample is initially injected into a biocompatible injection loop connected to this valve. After the sample is injected into the system, the valve is switched such that the sample loop is inserted into the sample flow stream in a manner similar to that in which normal high pressure liquid chromatography injection loops operate. When this occurs, the sample fluid within the sample loop is pushed into the sample/sheath convergence area by fluid being delivered from a liquid vessel at low pressures (typically 1–3 psi). This sample delivery typically occurs at flow rates in the range of about 0.01 to about 0.10 mL/minute.

Preferably, the biocompatible tubing is run through a length of stainless steel tubing that seals the biocompatible tubing so as to prevent any liquid, contaminants or air from passing up through the upper cytometer, thus compromising the biocompatibility of the system. In addition, the stainless steel tubing physically stabilizes the biocompatible tubing, which stabilizes the alignment of the tubing, and therefore, the sample core flow in the sheath fluid. A preferred method of sealing the system is to use a retaining part, such as an input seal nut, and an O-ring. In addition, the tubing may be sealed into a stainless steel tubing with an adhesive, such as a silicone sealant.

The O-rings that seal the tubing to the upper cytometer chamber serve to seal the sheath fluid in the chamber, but do not actually have contact with the sample fluid, which is continually swept away into the square bore capillary region immediately on its exit from the biocompatible tubing. The O-rings are compressed against the tubing and the upper cytometer chamber when the input seal nut is tightened into the threaded taps in the upper cytometer chamber. Placement of the sample input tubing concentrically within the sheath chamber is critical to having the sample core flow down the center of the square bore capillary. There can be any number of O-rings in the input seal nut. Preferably, there are at least two O-rings in the input seal nut which are sufficiently far apart so that the sample input tube cannot tilt enough to disturb this concentricity. A preferred separation is about 2 to about 4 mm. The stainless steel shroud around the biocompatible sample input tubing also aids in maintaining this concentricity. When necessary, it is possible to use set screws or other devices that tap into either the retaining means or the upper cytometer chamber and can be made to push against the sample input tube (or a reinforced housing around the sample input tube) in such a way as to guide it so it is concentric with the sheath chamber, for the purposes described above. Preferably, three screws set 120 degrees radially apart or four screws set 90 degrees radially apart are employed.

By employing a sample input system that is highly biocompatible, the sample only contacts biocompatible material, which aids in preventing irreversible bacterial adhesion on the interior surfaces of the sample delivery components. An illustrative example of a preferred biocompatible, chemically resistant material is polyether etherketone (PEEK). The use of PEEK materials almost completely eliminates unwanted adsorption of organisms onto the delivery components, which makes it possible to detect extremely small numbers of fluorescent objects at the limit defined by conventional sampling statistics. Thus, bacteria at very low levels (e.g., 1–1,000 organisms per ml) can be detected.

PEEK suppresses bacterial adsorption because it is both modestly hydrophilic (so it does not allow hydrophobic interactions to drive adsorption) and uncharged (so there is no electrostatic driving force for adsorption). It also has a fairly low surface energy with very few "reactive" functional groups present at its surface. Any materials with these properties are suitably "biocompatible" in the sense that they will have a reduced tendency to adsorb bacteria and prevent bacteria detection.

Furthermore, one of the main goals of this invention is the efficient delivery of the sample to the sampling chamber, where the detection region is located (i.e. where the core (sample) flow crosses the laser beam). The present instrument is constructed so that the sample is only exposed to biocompatible surfaces, such as PEEK, the entire way from its entry into the instrument until it reaches the detection region. Thus, all components may be made of PEEK or another suitable material, including junctions between tubing, bulkhead fittings where tubes cross walls in the instrument, etc.

An alternative, biocompatible delivery system, may still include materials such as metals and glass. A preferred metal is stainless steel (SS). These materials may still be used, once they are modified to be "biocompatible" in the sense described above. The iron in SS leads to the formation of iron oxide at the surface of SS. Due to normal metal oxide-based acid-base chemistry, SS turns out to be positively charged at neutral pH values, so negatively charged bacteria are typically strongly adsorbed at SS surfaces. However, it is possible to derivatize the surface of SS with any of a variety of coatings to endow it with "biocompatibility". One of the types of coatings that is especially biocompatible is polyethylene oxide-like polymers (i.e. $HO-(CH_2CH_2O)_n-OH$), known as PEO or PEG (polyethylene glycol). It is possible to buy or synthesize PEO and PEG derivatives that form chemical bonds at the iron oxide surface. These make the SS surface look like "water" since PEO is very water-like in its chemical properties. Since there is no hydrophobic driving force and no electrostatic driving force, this type of treatment will render the interior surface of SS tubing of other parts "biocompatible" in the sense described above. A similar method can be used for glass, where the use of silane reagents to attach PEO or other types of coatings to glass surfaces will render them less adsorptive toward bacteria.

The flow cytometer is constructed to be simple and rugged. It employs a glass capillary that has no optical interfaces in the line of sight of the detector. Preferably, a square bore capillary is used. In this fashion, background scattering, such as would occur when the sample is impinged onto a flat glass sheet, is essentially eliminated.

A further preferred feature employs a mechanically rugged holder for the square bore capillary so as to accommodate a relatively thin-walled square bore capillary. The use of such thin-walled capillary tubes not only decreases the expense, but also tends to optimize the optics and detection due to lessened scattering and the like. In addition, the inner diameter of the capillary tube must be at a distance such that there is not excessive reagent consumption due to the higher volumetric flow rates. Conversely, the inner diameter of the capillary tube cannot be so small that it is too difficult to the laser beam cleanly into the capillary tube without colliding with the walls. Ideally, the capillary tube's inner diameter will be from about 1 mm to about 20 microns. An illustrative square bore capillary has a 500 micron interior diameter. Yet another aspect of the holder is a design which allows the square bore capillary to be easily removed and replaced, requiring minimal realignment of the optical components of the system.

The cytometer chamber assembly handles and controls the flow of sample and sheath fluids to be analyzed. The cytometer is designed to control a very small sample stream by capturing it into a larger sheath stream. When the sample is entrained in the sheath stream, it is protected from outside contamination and possible degradation. However, the main purpose is to control the velocity of all particles or material of interest in the sample. This makes them all pass through the laser beam at the same rate. It also gets the sample core away from the walls, thus minimizing wall scattering. The sample stream is introduced into the center of the sheath stream. Controlling the flow rate of the sample and sheath stream allows management of the velocity of the sample stream and size control of the sample core diameter. The present invention allows the user to run flow rates that are a factor of 10–100 slower than those used in conventional flow cytometers.

The flow-through cytometer chamber assembly, optics, and optical path are components which work in concert to direct and control the sample stream through the cytometer assembly and illuminate the bacteria or other contaminant for detection and counting.

A preferred embodiment provides for the adjustment of the flow-through cytometer assembly to insure optical alignment and adjustment of the sample stream for proper-location within the sheath flow. The entire flow-through cytometer assembly can be rotated about its axis to provide optical alignment for the "square-bore chamber" with the laser.

Thus, the invention is easily able to achieve the proper alignment, between the laser signal input and the sample path as it flows through the square bore tube capillary. Proper alignment is needed to provide satisfactory accuracy of measurement and the like. The ease with which such proper alignment can be achieved is likewise important so as to facilitate use of the equipment.

To this end, an embodiment of this invention utilizes a mask positioned adjacent the face of the square bore capillary in the path of the laser signal input to such capillary. Desirably, the mask is positioned vertically down the capillary face, providing a vertical slit with a width slightly greater than that of the laser signal. The mask can be made of any material that prevents the laser signal from passing therethrough. Indeed, if it is desired, even black tape or the like can be employed for the mask.

In this fashion, alignment is facilitated because the location of suitable laser signals can be visually seen in relation to the position of the sample. Adjustment of either the position of the laser signal or that of the sample can be made to readily achieve proper alignment. Another function of the mask is that it be centered on the square bore and larger than the sample "core" flow. In this way, with a sufficiently powerful light source, one need not actually align the laser with the core flow. Rather, one need only align enough to get the light through the mask, meaning that it must also impinge on the sample core flow.

The flow-through cytometer chamber assembly can be designed to provide many capabilities, including, but not limited to: quick change-out features for fast and easy replacement of the entire cytometer assembly, tapered locating pin to provide accurate relocation, and quick connections for sheath and flow samples.

In addition, the flow-through cytometer chamber assembly provides a durable or "hardened" support system for the delicate glass capillary tube. This is accomplished by providing a design where the glass capillary tube chamber is secured in the upper cartridge portion of the assembly. Optionally, pins or rods secure the upper and lower portions of the cartridge. Preferably, stainless steel pins are used. Moreover, the glass capillary tube is preferably secured in the upper cartridge portion with O-rings for shock protection and sealing. Thus, the glass capillary tube remains effectively isolated from the lower cartridge providing additional protection. Finally, the flow-through cytometer chamber assembly provides a "sealed system" to prevent leakage of a contaminated sample.

Referring now to the figures, several embodiments of this invention are provided.

FIG. 1 describes the Cytometer Chamber Assembly. Upper cytometer chamber 1 houses sample input port 4, sheath input port 7, and the sample/sheath convergence area 8. The upper cytometer chamber 1 serves as the mounting point for the optional support rods 3. The support rods 3 must be very stiff to prevent loading on the glass parts. High strength metal and stiff plastics, for example, are suitable materials for the support rods. The lower cytometer chamber 2 is optionally attached to support rods 3. The lower cytometer chamber 2 provides a sealing surface and protection for the square bore glass tube 6. The upper cytometer chamber 1 uses the sample/sheath convergence area 8 to manage the sample and sheath input ports 4 and 7 and insures proper placement of the sample flow within the sheath flow.

Lower cytometer chamber 2 supports and protects the glass tube 6 and guides the assembly into the drain cup (not shown) and provides a sealing surface for the drain. Optionally, the lower cytometer chamber 2 is attached to the upper cytometer chamber 1 with support rods 3. As a unit, the upper cytometer chamber 1 and the lower cytometer chamber 2 make up a "cartridge" that can be easily replaced or cleaned, plus protect the delicate glass tube 6 from damage.

Sample input tube 4 is usually a selection of plastic tubing secured inside a section of a rigid and hard material. Illustrative examples include a hypodermic needle, a stiff plastic or a piece of high strength metal, such as stainless steel. This rigid and hard tubing provides support, improves straightness and a sealing surface to prevent leaks. The sample input tube 4 is held in place with the input seal nut 5 and sealed with O-rings (not shown). The sample input tube 4 is centered over the sample/sheath convergence area 8 so as to deliver samples into the sheath fluid stream.

Figure 2A:
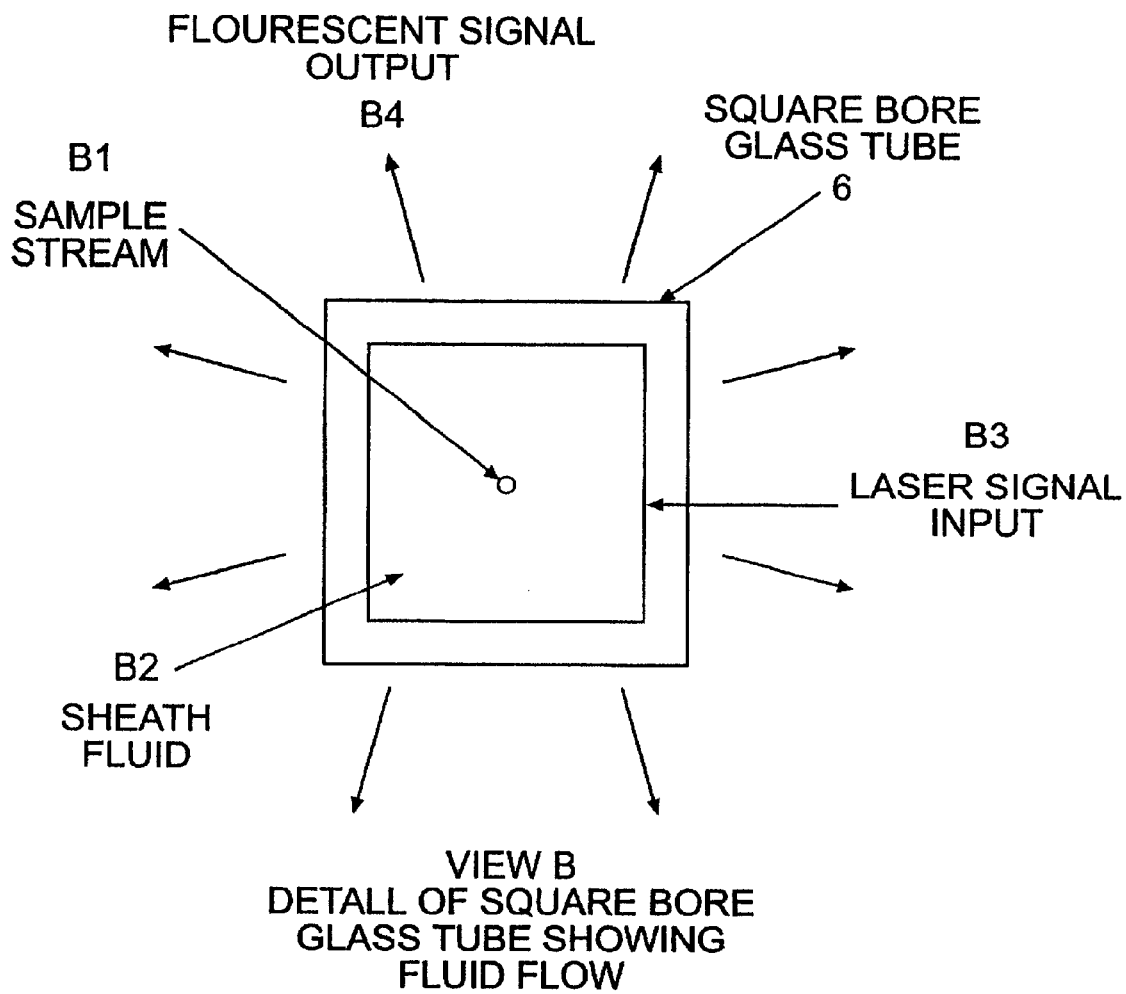
FIG. 2B is a cross-sectional view taken generally along Section A—A of FIG. 1 and shows the lower glass tube assembly; View B in FIG. 2A illustrating in detail the square bore capillary and the location of the sample steam in such capillary as well as the location of the laser signal input relative to that of the fluorescent signal output.
Figure 2B:
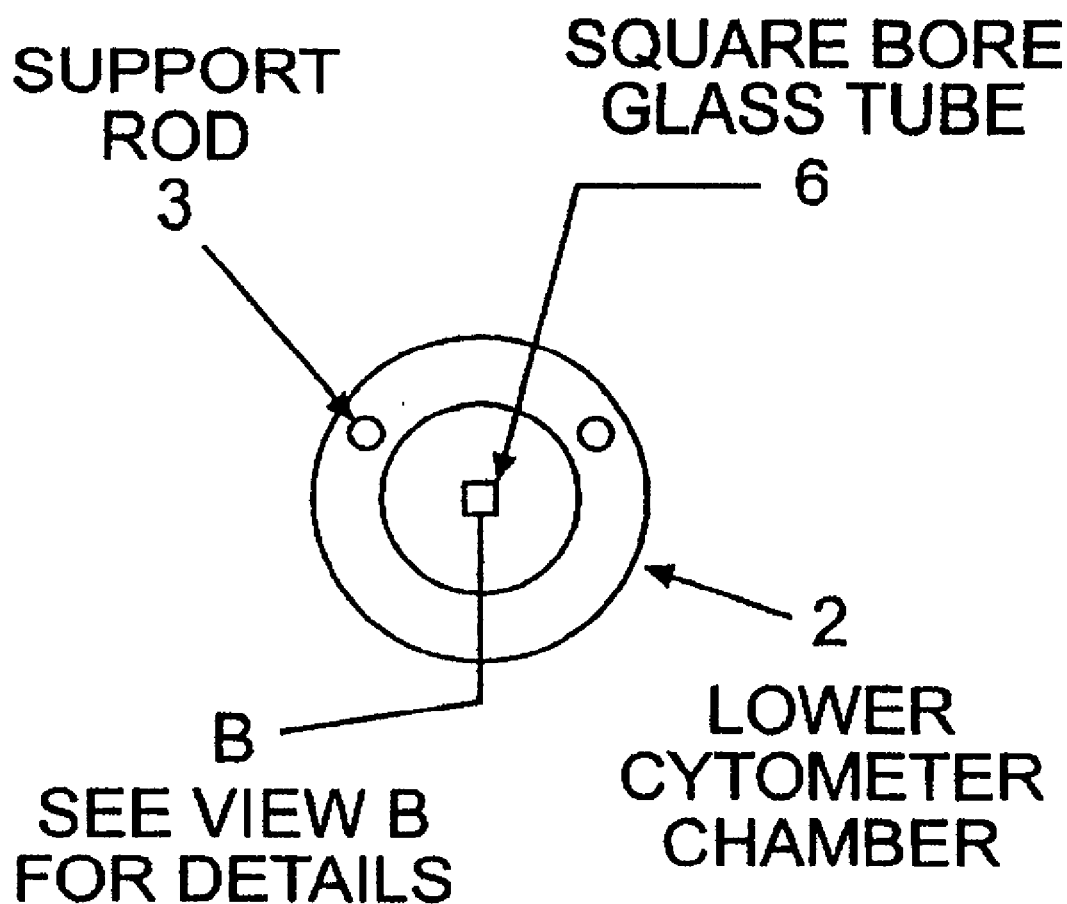

A top view of the lower cytometer chamber 2 and a section view of the support rods 3 is illustrated in FIGS. 2B and 2A, respectively. The square bore glass tube 6 with a cross-section of the sample/sheath flow is shown in an enlarged view (View B). When the unit is operating, the sample B1 is surrounded by sheath fluid B2. The sheath fluid B2 provides containment and protection of the sample B1 as it flows through the square bore glass tube 6. While the sample B1/sheath flow B2 are in the square bore glass tube 6, the laser signal B3 is focused on the sample B1 stream. Under proper conditions (determined by the chemistry of the sample), fluorescent signals B4 are emitted and picked by a photomultiplier tube or other appropriate detector.

A sample enters the top of the upper cytometer chamber 1, as illustrated in FIGS. 3A, 3B, 3C and 3D, through the sample fluid input port 4. The terms sample fluid input port and sample input tube are used interchangeably. The sample may be delivered at a rate, for example, of about 0.01 to about 0.1 mL/minute. The pressure heads used to drive them may control the flow rates, which is typically 1–3 psi. In addition, surfactants may be used to control the viscosity and surface drag in the delivery tube. By using slower, controllable flow rates, a well-defined and reproducible flow rate in the tubing is produced, especially when the sample itself contains surface active compounds that would adsorb and influence the surface conditions in the tube and therefore the flow rate. The sheath fluid enters the chamber through the sheath fluid input port 7. Note the sheath fluid is perpendicular to the sample fluid. Sheath fluid is usually delivered at a rate, for example, of about 1 to about 30 mL/minute. A typical sheath fluid rate is 5 mL/min. This value may change depending on sample properties.

As one illustrative example, the upper cytometer chamber may have the following approximate geometric specifications:

Inside diameter 0.156 in. (refer to dimension ID 1)
Inside diameter 0.040 in. (refer to dimension ID 2)
Distance 0.250 in. (refer to dimension Dist 3)
Inside angle=30°
Diameter of sample tube=0.08 in.

Figure 3A:
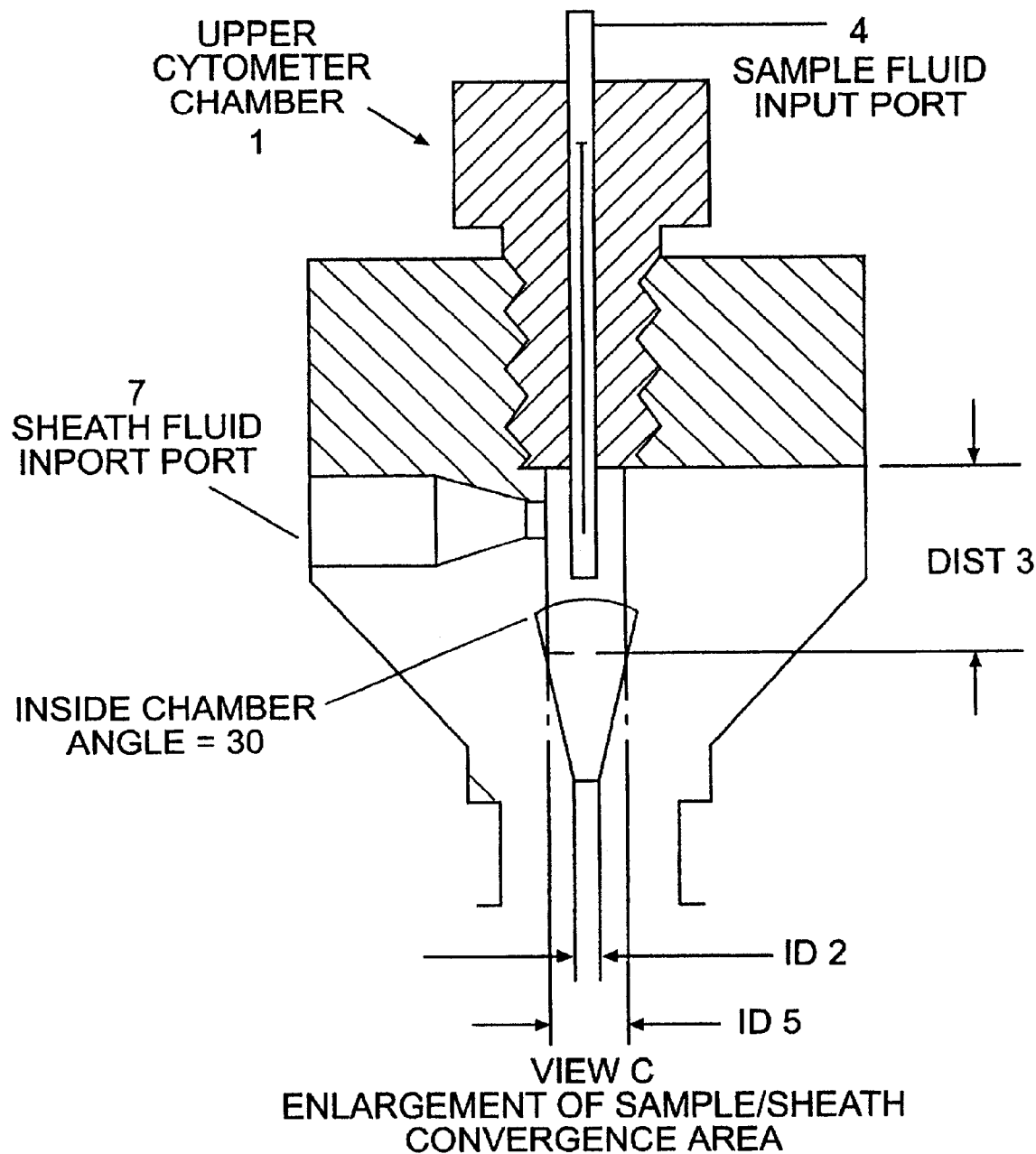
FIGS. 3A and 3B show an enlarged view of the sample/sheath fluid convergence area in the upper cytometer chamber of the preferred embodiment; View C being an enlargement of such convergence area.
Figure 3B:
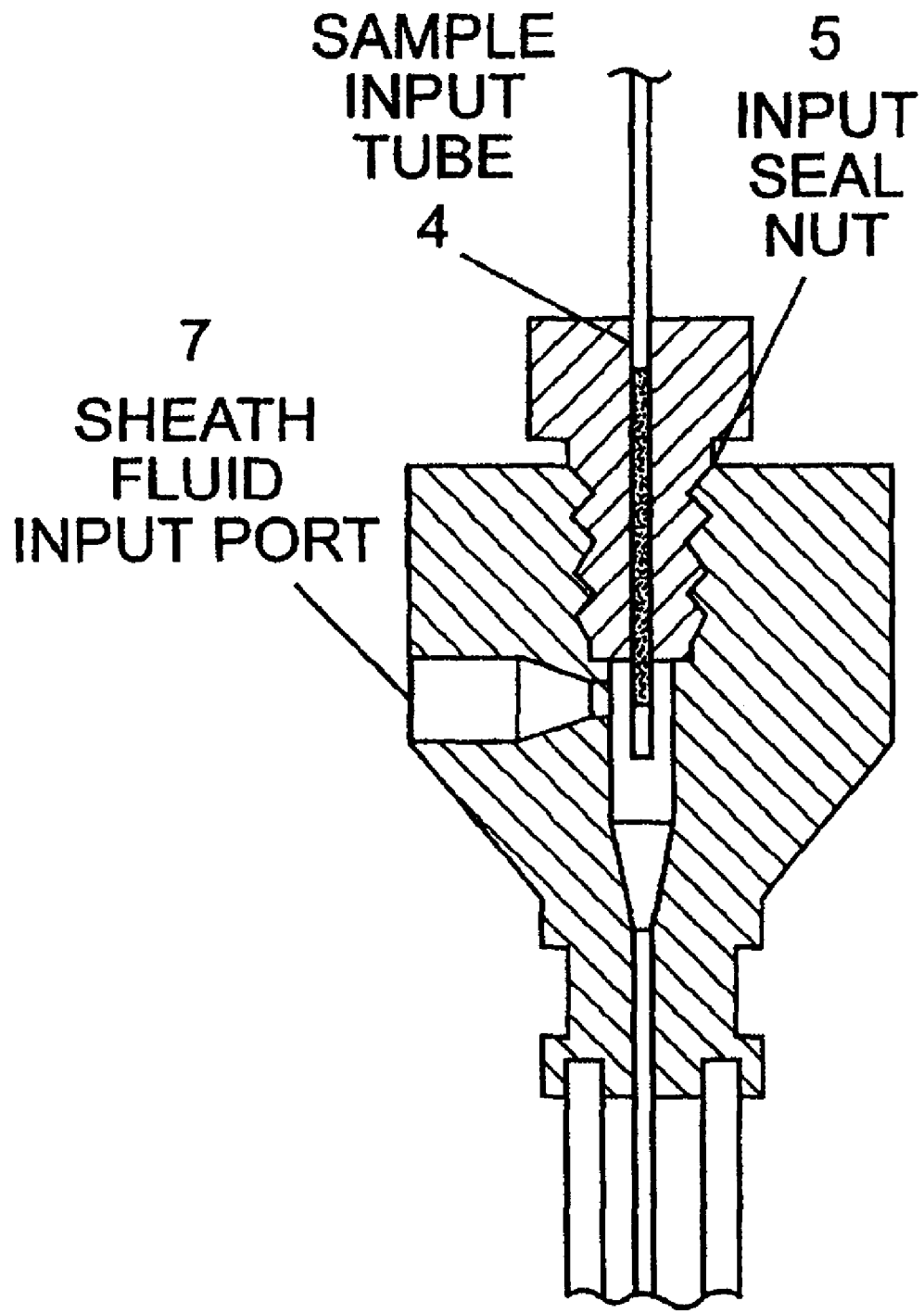
Figure 3C:
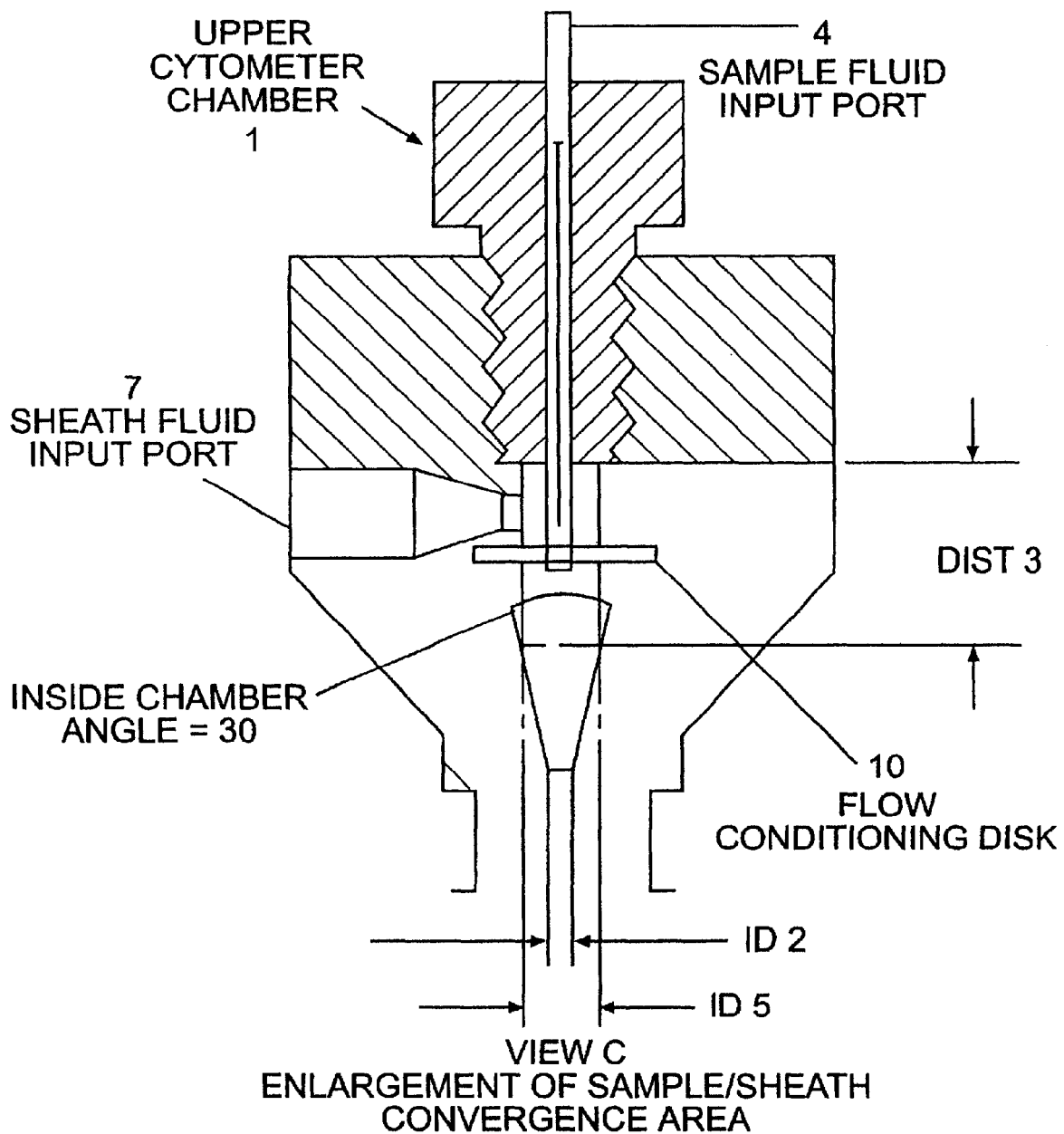
FIGS. 3C and 3D show another embodiment similar to FIGS. 3C and 3D, except utilizing a flow conditioner disk.
Figure 3D:
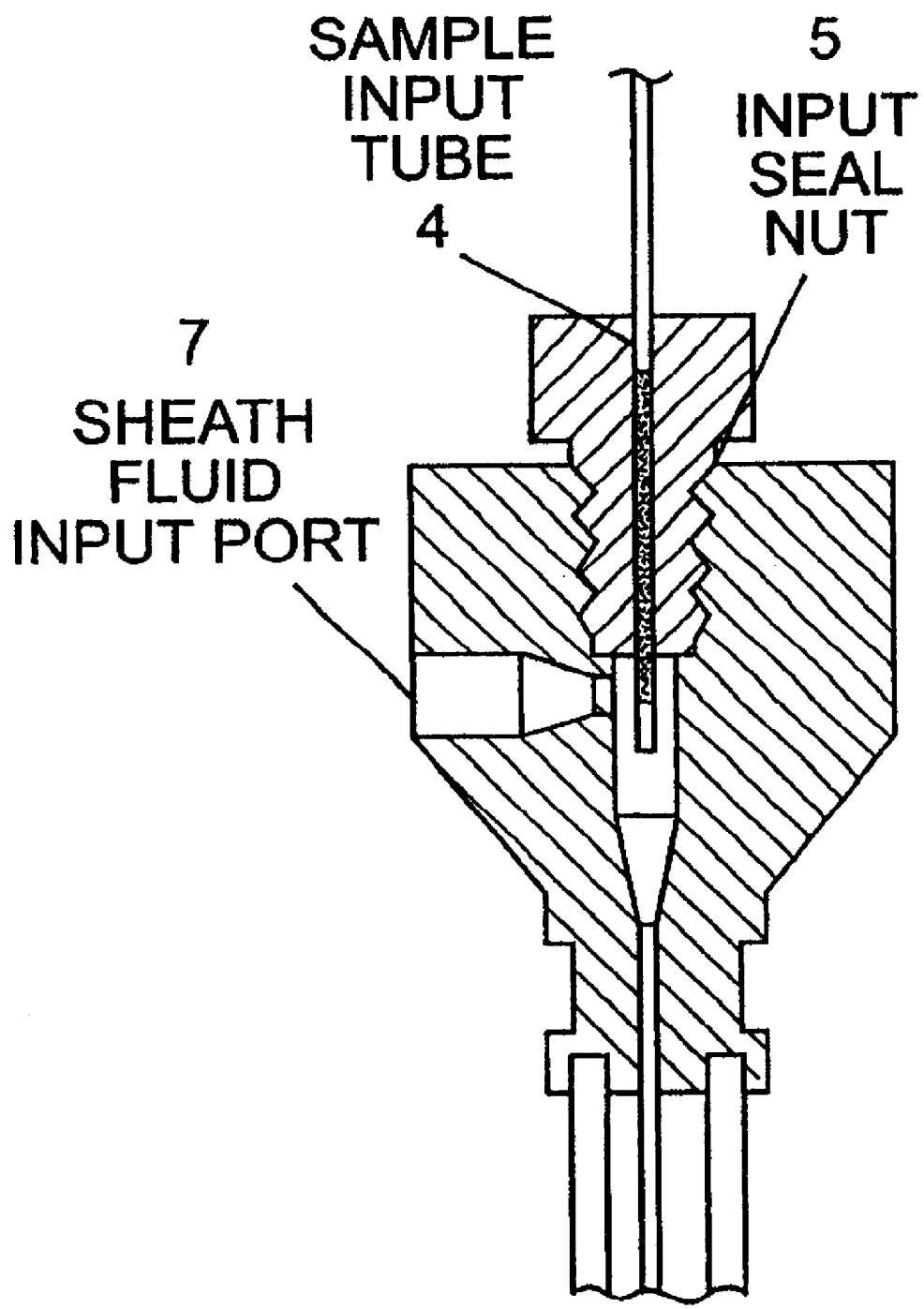

In one preferred embodiment shown in FIG. 3C, a flow conditioner disk 10 is utilized. This directs the sheath flow input such that there is a laminar flow condition around the sample inlet tube.

Figure 4A:
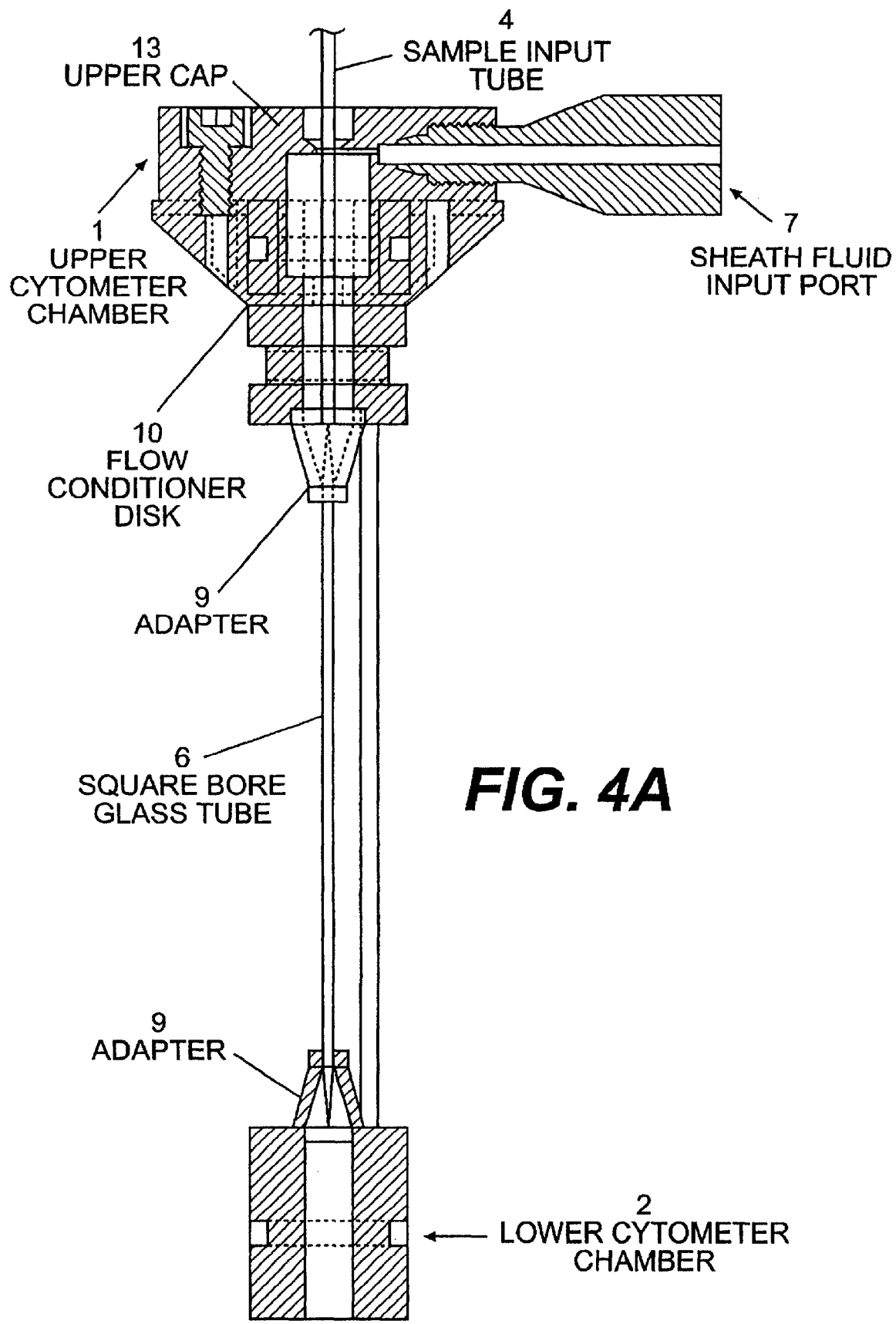
FIGS. 4A and 4B show an embodiment of a cytometer chamber assembly utilizing a flow conditioner disk and adapters for the glass tube assembly.
Figure 4B:
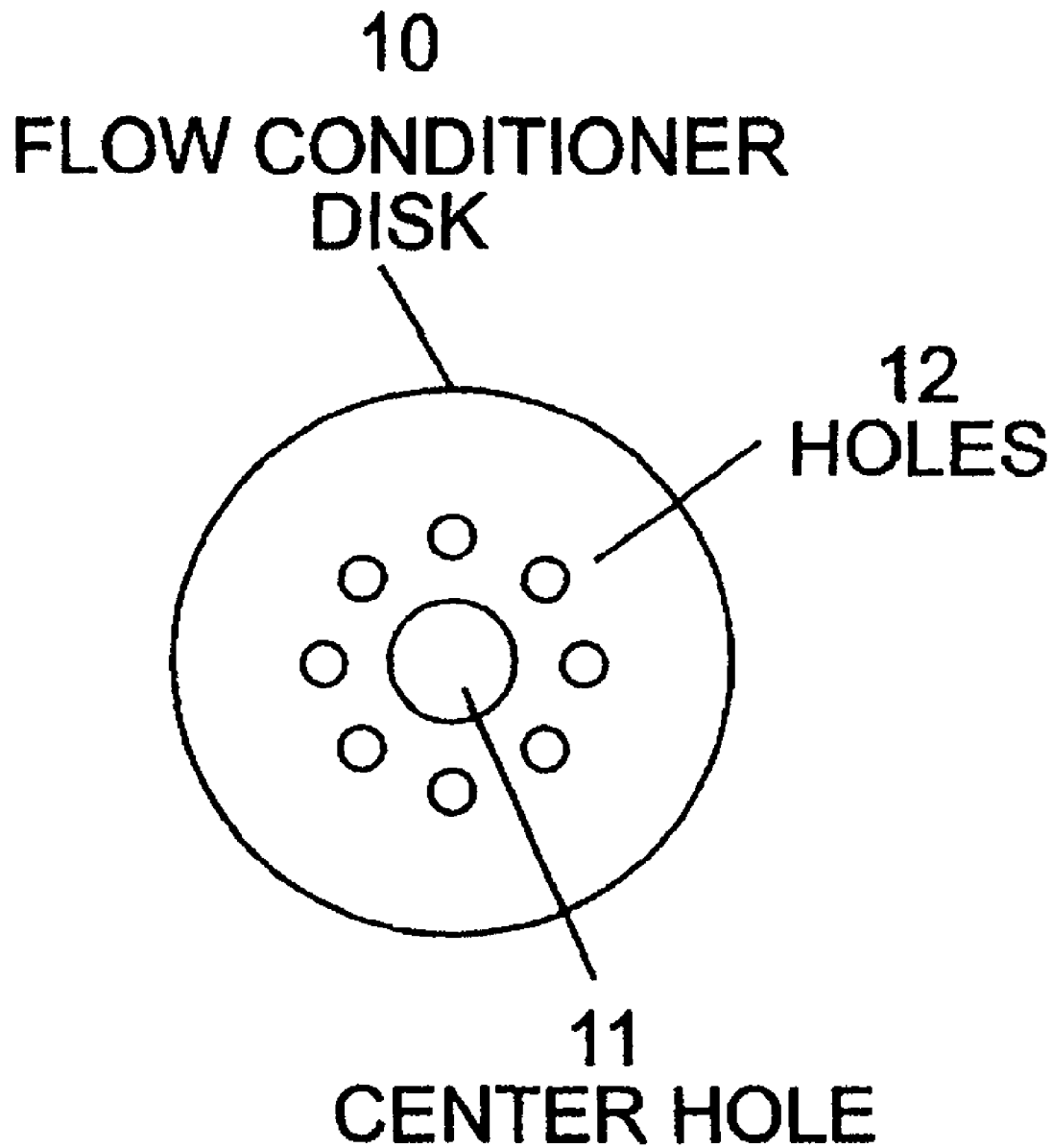

The cytometer chamber assembly shown in FIGS. 4A and 4B uses a removable flow conditioner disk 10. This flow conditioner disk 10 is placed just below the sheath fluid input port 7. This disk 10 has a center hole 11 to support and guide the sample input tube 4, plus a series of small holes 12 around the sample input tube 4 to direct the sheath input fluid into the main flow chamber. Appropriate sizing and spacing of the holes 12 will straighten the incoming sheath fluid as it flows into the main flow chamber. The disk 10 thickness may be adjusted to provide additional control of the sheath fluid. This disk 10 can be removed for cleaning and inspection. In addition, geometry of this disk 10 can be adjusted for optimum fluid flow depending upon fluid viscosity, flow rate and velocity.

The illustrated upper cytometer chamber cap assembly 13 is attached with threaded fasteners and can be rotated incrementally to accommodate the sheath fluid input port 7. The threaded fasteners are used to apply pressure to the O-ring so that it seals the top part of the chamber to the bottom part of the chamber. Other attachment or retaining means may be used so long as they apply pressure on the O-ring, thereby sealing the top part of the chamber to the bottom part of the chamber. Further, as can be seen, adapters 9 (e.g., injection-molded plastic) are provided for the upper 1 and lower chamber 2 assemblies that allow ready alignment of the glass tube 6. An alternative embodiment can include the use of a glass or quartz adapter attached to the upper end of the glass tubing. The upper adapter could then be fused to the upper end of the glass tubing. This would create a single piece of glass that performs the function of tapering the sheath fluid and providing a direct pathway into the square bore tubing at the bottom.

Any known collection or drain device may be utilized to collect the sample and sheath fluid after passing through the cytometer.

Figure 5:
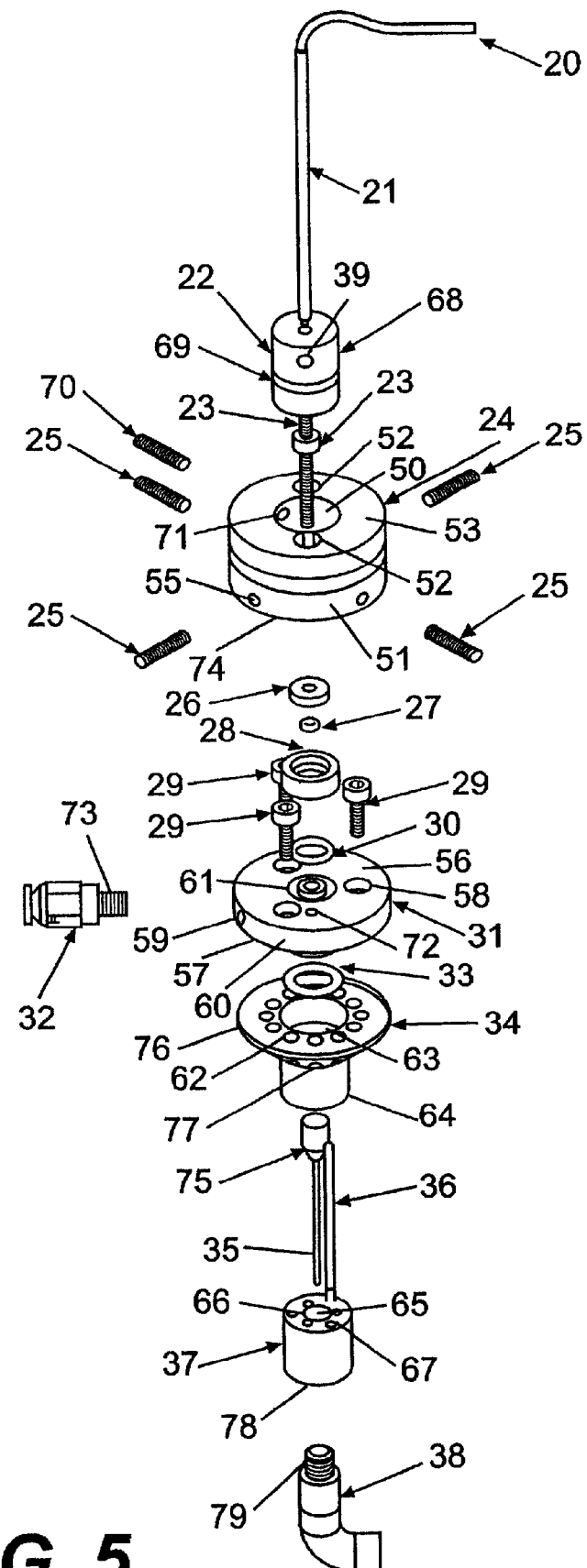
FIG. 5 shows a preferred embodiment of the biocompatible cytometer chamber assembly.

A particularly preferred embodiment of the biocompatible cytometer chamber assembly is illustrated in FIG. 5. The biocompatible cytometer chamber assembly has both an upper chamber assembly and a lower chamber assembly. The upper chamber assembly can be broken down into three sections top chamber section 24, middle chamber section 31, and bottom chamber section 34. A biocompatible tube 20 is contained within a rigid structure 21 (to form a "needle and tube assembly") and inserted into a retaining mechanism 22. The retaining mechanism 22 includes at least one opening 39, which extends from the outer periphery 68 to the inner periphery 69. This allows a screw (not shown) to be inserted through the opening 39 to secure the needle and tube assembly 21 inside the retaining mechanism 22. In addition, retaining mechanism 22 contains a recess 69 extending around the outer periphery 68. The retaining mechanism 22 engages top chamber section 24. The retaining mechanism 22 is configured and dimensioned such that the needle and tube assembly 21 fits snugly into an inner periphery 50 of the top chamber section 24. Preferably, the retaining mechanism 22 is held in place in the top chamber section 24 by one or more set screws 70 or the like. Set screw 70 is inserted through opening 71 which extends from outer periphery 51 to the inner periphery 50 of top chamber 24 and presses against the retaining mechanism 22, at recess 69, until a snug fit is accomplished or the desired sealing is achieved.

As can be seen from FIG. 5, there is provided one or more openings 52 that run through the top surface 53 of top chamber section 24 to the bottom surface 74 for the passage of connecting joints (e.g., screws) 23 to connect said top chamber section 24 to middle chamber section 31. In addition, the top chamber section 24 can be fitted with screws 25, which aid in steering alignment disk 28 in a concentric manner. Preferably, the screws 25 are inserted through openings 55 on the outer periphery of the top chamber section 24, such that the screws 25 or the like, are able to extend through the openings 55 in a sufficient length so as to contact the alignment disk 28 and provide stability thereto. In addition, underneath the top chamber section 24, there is located a flow disk insert 26 to prevent turbulent flow. The flow disk insert 26 is situated inside the alignment disk 28, which is positioned within top chamber section 24. The combination of flow disk insert 26 and alignment disk 28 work to provide laminar flow which is needed to give a stable sheath/core arrangement. Preferably, an O-ring 27 is placed between the flow disk insert 26 and the alignment disk 28, thereby providing a sealing between the disk insert 26 to the alignment disk 28, and the needle and tube assembly 21. Accordingly, the disk insert 26, O-ring 27, and the alignment disk 28 have openings through the center of each such that said disks 26 and 28 and O-ring 27, may support and guide the needle and tube assembly 21. Additionally, an O-ring 30 resides in opening 61 beneath the alignment disk 28 to aid in sealing the alignment disk 28 to the middle chamber section 31. O-ring 30 also seals the closure around needle and tube assembly 21.

The middle chamber section 31 is fitted with openings 72 that run from the top portion 56 to the bottom portion 57 such that the top chamber section 24 and middle chamber section 31 can be coupled with one another. The coupling is achieved by inserting screws 23 though openings 52 in top chamber section 24 and into openings 72 in middle chamber section 31.

The middle chamber section 31 includes an inlet 59 for a sheath input port 32 to be attached. The inlet 59 runs from the outer periphery 60 to the inner periphery 61 of middle chamber section 31. Preferably, the sheath input port 32 is coupled to the middle chamber section 31 via threaded means 73.

The middle chamber section 31 preferably contains at least one opening 58 that runs from the top portion 56 to the bottom portion 57 such that fastening joints 29 can be inserted through the openings 58 so as to connect the middle chamber section 31 to the top chamber section 24. Preferably, the middle chamber section 31 contains several openings 58 for the fastening joints 29. The middle chamber section 31 engages a bottom chamber section 34 by fastening means such as set screws 29 in the provided openings 62. Additionally, an O-ring 33 is placed between the middle chamber section 31 and the bottom chamber section 34 to aid in sealing the system. Preferably, openings 62 in bottom chamber section 34 are provided to give some latitude in the rotational placement of the bottom chamber section 34, glass tube 35, support rods 36, and lower chamber 37 with respect to middle chamber section 31. Openings 62 extend from top portion 76 through to middle portion 77 of bottom chamber section 34. This is accomplished by inserting screws 29 through an opening 58 in middle chamber section 31and an opening 62 of bottom chamber section 34. Generally, the screws 29 do not extend out of the middle portion 77 of bottom chamber section 34. Ideally, the screws 29 or other fastening means will be inserted through holes 62 a sufficient distance to hold bottom chamber section 34 tightly against middle chamber section 31. Preferably, bottom chamber section 34 has a plurality of openings 62, such that bottom chamber section 34 can be rotated until it enjoys a tight and concentric fit with middle chamber section 31. At the point the desired fit is met, the screws 29 will be inserted into openings 62.

The bottom chamber section 34 is such that the opening through the center 63 is configured and dimensioned with the opening 61 in the middle chamber section 31 and the opening 50 in top chamber section 24 and are such that they maintain the concentricity of the system.

The lower portion 64 of the bottom chamber section 34 is configured and dimensioned to receive and guide a glass tube 35. Accordingly, the glass tube 35 is aligned below the bottom chamber section 34 so as to maintain the concentricity of the invention. This alignment allows the sheath fluid and sample to continue in an uninterrupted path through the system. Preferably, the glass tube 35 will be configured and molded such that the top part of the glass tube 35 is tapered 75 to interface and seal with the lower portion 64. A preferred embodiment of this interface is to further seal the tapered 75 section of the glass tube 35 to the lower portion 64 with epoxy resin. The glass tube 35 extends from the lower portion 64 of the bottom chamber section 34 to an opening 65 in optional lower chamber 37. The lower chamber 37 is also configured and dimensioned to receive and guide the glass tube 35. The inner periphery 66 of lower chamber 37 provides a sealing surface and protection for the glass tube 35. In one embodiment, to further insure that the glass tube 35 is sealed to the inner periphery 66 of lower chamber 37, an epoxy or similar substance is used to seal the glass tube 35 to the lower chamber 37.

Figure 6:
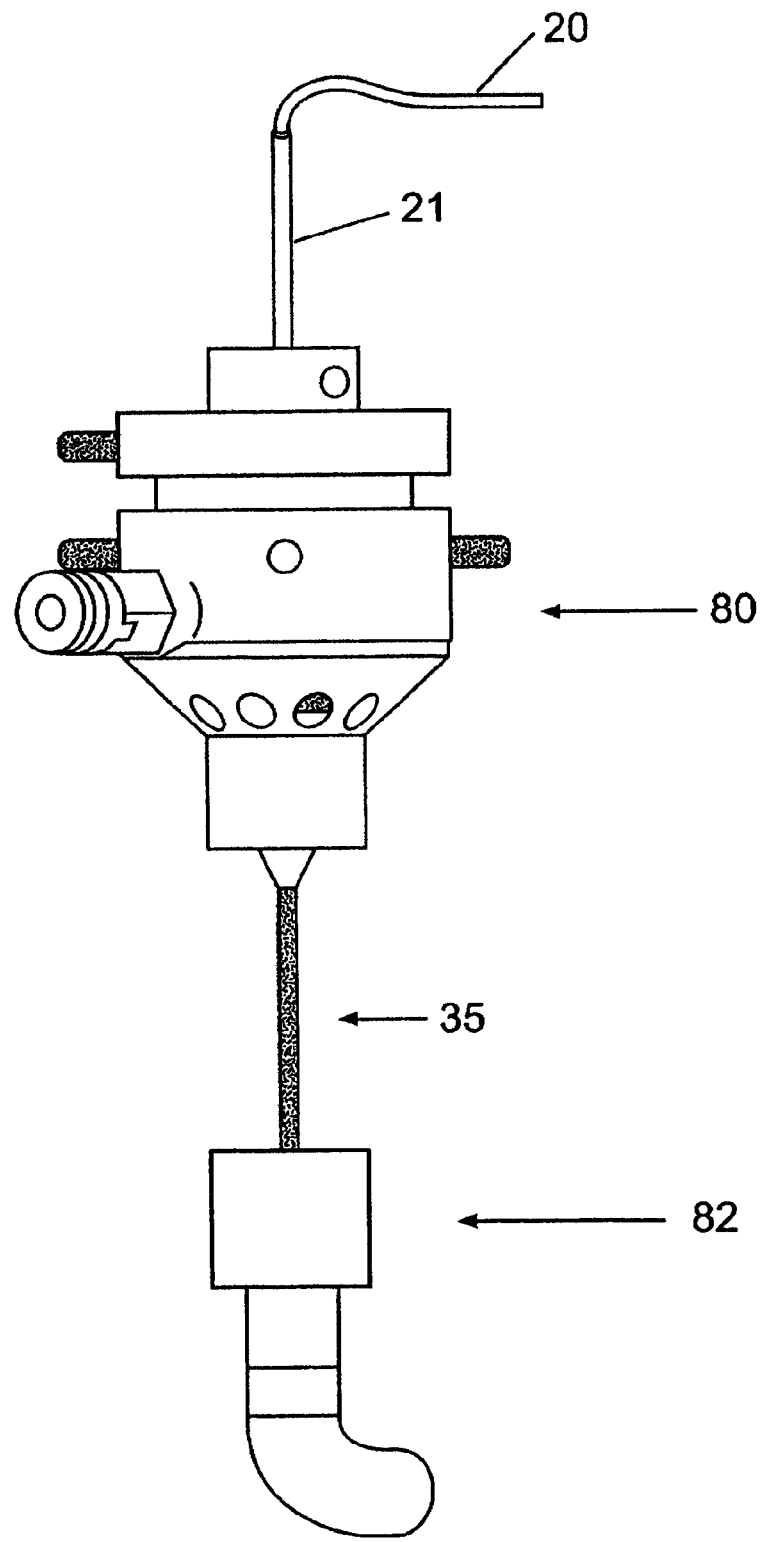
FIG. 6 is a side elevation view of the cytometer chamber assembly.

The top portion 64 of lower chamber 37 is provided with openings (not shown) and the lower portion 64 of bottom chamber section 34 are provided with openings 67 that allow for the optional placement of one or more support rods 36 between the lower chamber 37 and bottom chamber section 34. On a lower portion 78 of the lower chamber 37 a connection device 38 can optionally be attached by fastening means 79 to facilitate the draining of the glass tube 35. Similar to the As shown in FIG. 6, the biocompatible tube 20 is contained within the rigid structure 21 (to form a "needle and tube assembly") and placed into an upper chamber assembly 80. The upper chamber assembly 80 is configured and dimensioned to allow the glass tube 35 to be inserted into said upper chamber assembly 80. The combination and orientation of the upper chamber assembly 80, the glass tube 35, and the lower chamber assembly 82 is such that they are able to maintain a concentric flow of the sample and sheath fluid.

Figure 7:
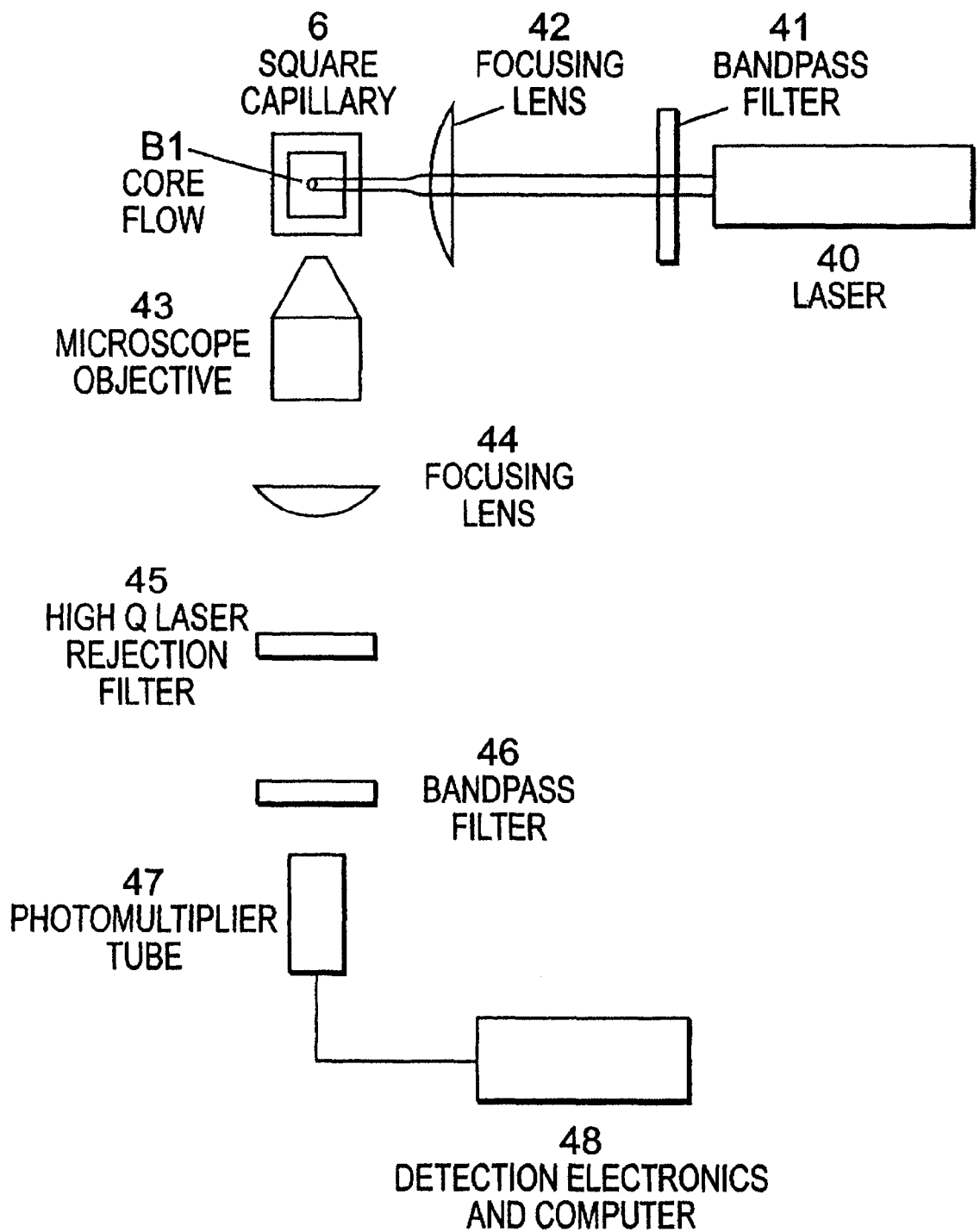
FIG. 7 illustrates a preferred embodiment of an optimized optical system for carrying out the monitoring/detection function.

In regards to the optical components and optical path, as illustrated in FIG. 7, preferably a low-powered laser 40 provides source light for the system, but the output from a high powered light source after passing through a wavelength selector 41 (e.g., filter) could also be used. The laser light is refined by a narrow bandpass filter 41 to eliminate unwanted wavelengths and then focused into the square-bore tube 6 with a lens 42. A system of XY translators may be used to position the square-bore tube 6 relative to the objective pickup lens 43 and the light source 40. In addition, the laser can be adjusted by using screws in the front and back of the laser housing that cause the laser housing to pivot on a pair of ball bearings that are under the middle of the laser housing. This will align the beam with the core flow B1 (which is the sample stream) at the appropriate vertical position. In addition, the square-bore tube 6 can be rotated about its axis to optimize alignment or be moved up or down to optimize flow characteristics.

Particles suspended in the fluid passing through the square-bore tube 6 will cause light to scatter. The light scattered by the particles is the same wavelength as the source. In this instrument, scattered light of the same wavelength is actually an unwanted signal. Any same wavelength light scattered at 90° to the input laser signal is picked up by the 40× objective lens 43 and further refined by the plano-concave focusing lens 44, but is eliminated as a signal by the combination of the 633 nm or 650 nanometer laser cutoff interference (high Q bandpass) filter(s) and the 670 nanometer bandpass color filter 46.

The laser source light wavelength is selected to interact with marked bacteria and cause them to fluoresce at a wavelength different and always longer than the source. A portion of the fluorescent signal is also picked up by the 40× objective lens 43 and refined by the plano-concave focusing lens 44. The high Q bandpass filter 45 is selected to allow passage of the fluorescent signal.

The pulses emitting from the marked bacteria as they briefly pass through the laser beam can then be detected by any appropriate means, such as via a photomultiplier tube 47 and detection electronics and a computer 48.

With respect to illustrative examples of suitable components, a 500 µm square bore capillary made of fused silica can be employed. Exemplary lasers are 12 mW and 30 mW diode lasers at wavelengths of 650 nm and 635 nm. The detector may comprise a single photon-counting module, as is commercially available. A photomultiplier tube or avalanche photodiode, with the appropriate detection and control electronics for each case, may also be used.

Further, when it is desired to sample beer to avoid possible bacterial spoilage due to the presence of undue levels of *Pectinatus cerevisiiphilus*, the bacteria can be labeled with a commercially available "CY-5" labeled antibody (Jackson ImmunoResearch) and excited with a laser at 650 or 635 nm.

Figure 8A:
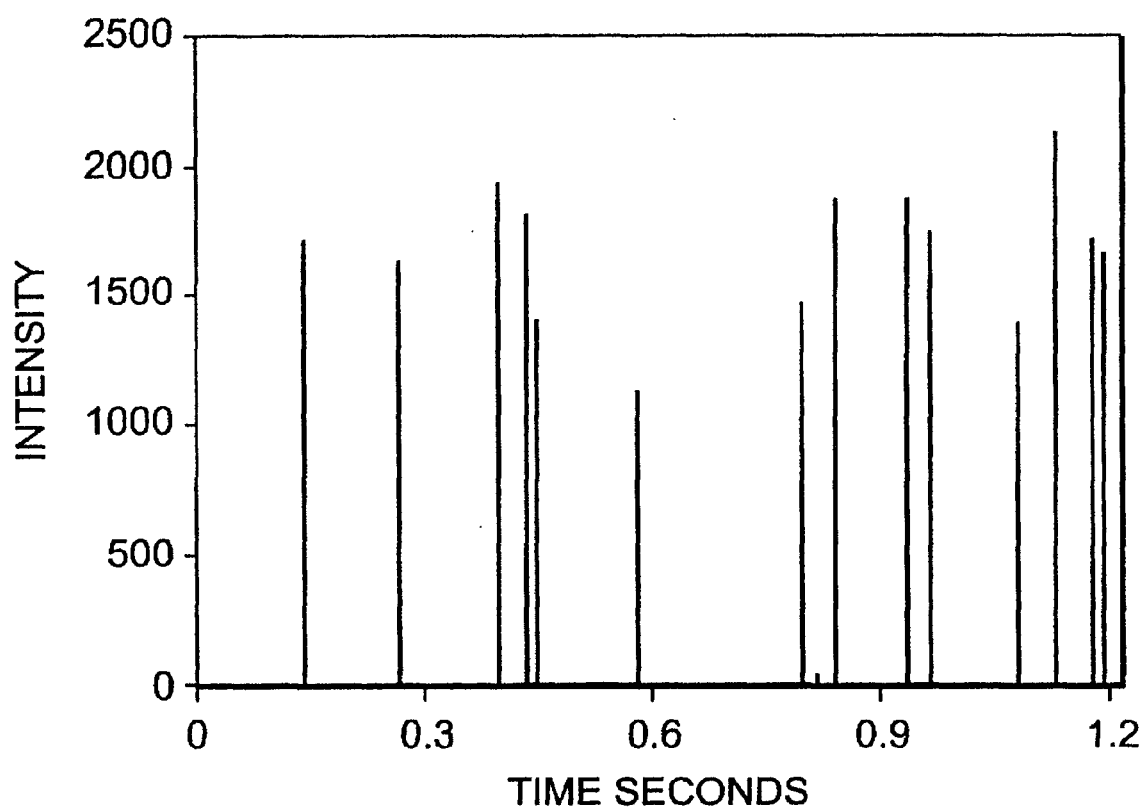
FIGS. 8A and 8B show two plots of intensity versus time obtained by analyzing samples of varying, known bacteria levels.
Figure 8B:
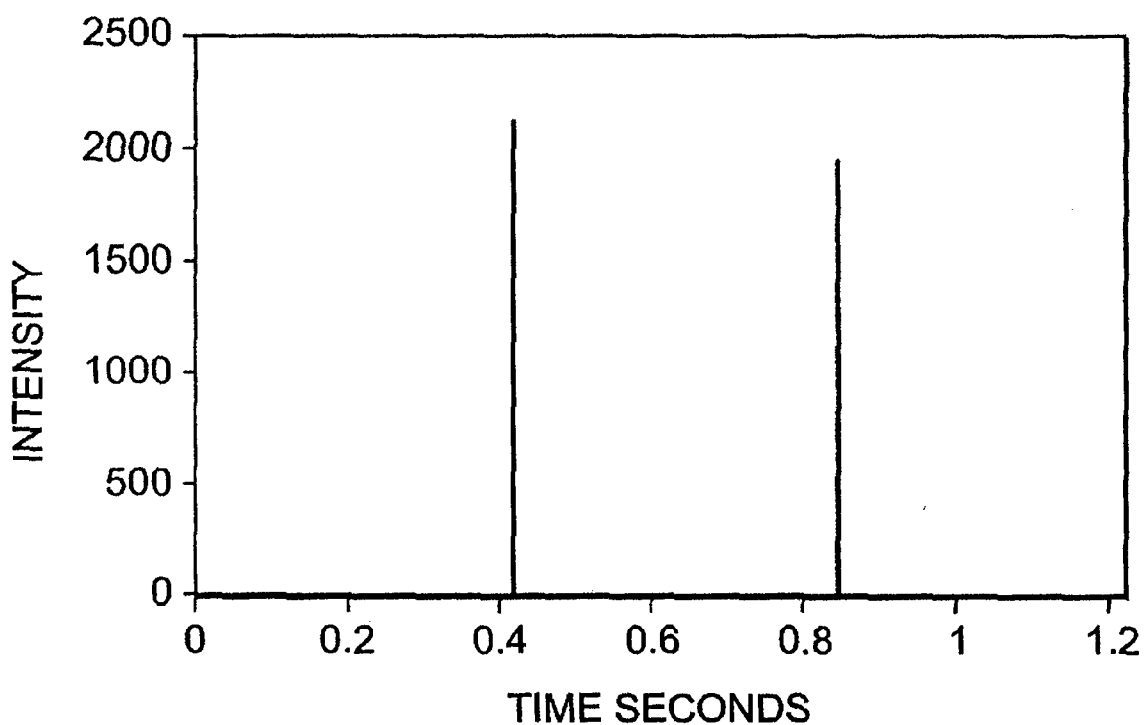

FIGS. 8A and 8B show two representative sets of data obtained for beer samples having bacterial concentrations of $10^4$ and $10^3$ bacteria per mL. The signal levels were about 1500 fluorescent counts during the 50 to 100 µsec. time in which the bacterium is within the detection region with a background level of about 10 counts, providing a signal-to-noise ratio of about 150:1.

The data plotted in FIGS. 8A and 8B show that the number of bacteria observed is directly proportional to the number of bacteria in the sample. The upper plot shows a portion of a 20 µL injection from a sample having about $10^3$ bacteria per mL, the lower plot being from the same-sized sample having about $10^2$ bacteria per mL. The sample flow rate, delivered to the sheath flow chamber for both samples was 0.07 mL per minute. The sheath flow rate was about 15 or 20 mL/min, and the fluorescent counts are binned in 150 µsec. increments.

In the upper data set, 17 bacteria are observed. In the lower data set, 2 bacteria are observed, as would be expected from the 10-fold dilution (within the statistical variation expected for stochastic data sets with such small numbers).

As can thus be seen, the timescale for monitoring/detection can be carried out in a few minutes while achieving a relatively high signal-to-noise ratio with a high level of sensitivity.

We claim:

1. A flow through detection apparatus for liquid samples comprising:
    means for introducing a fluid sample into a flowing sheath fluid whereby said sample is contained within biocompatible surfaces before introduction into the fluid sheath;
    means for detecting the fluid sample's contents; and
    means for directing the fluid sheath.

2. The detection apparatus of claim 1 wherein said means for introducing a fluid sample comprise:
    a biocompatible sample input system;
    a chamber attached to said sample input system by a sealing mechanism; and
    a sheath fluid input port attached to said chamber such that it creates an entry point for sheath fluid.

3. The detection apparatus of claim 2 wherein said sealing mechanism comprises:
    an input seal nut attached to the chamber by threaded attachment means and
    at least one o-ring being held firmly in position against both the input seal nut and the input system, thereby creating an impermeable barrier between the input system and the chamber, and further allowing the input system to extend inside of the chamber.

4. The detection apparatus of claim 2 wherein said means for directing the fluid sheath comprise:
   a rigid elongated tube fixedly attached to said chamber so that the fluid sheath passes within the tube.

5. The detection apparatus of claim 2 wherein said biocompatible sample input system is selected from the group consisting of glass, metal or plastic.

6. A biocompatible, adjustable flow-through system for detection, having an upper chamber which comprises:
   a biocompatible sample input tube, a sheath fluid input port, a retaining means, and means for interfacing with a glass tube;
   a glass tube for flow interfaced with said upper chamber; and
   a means for detecting contaminants in said flow.

7. The biocompatible, adjustable flow-through system for detection of claim 6 further comprising a lower chamber with means for interfacing with the glass tube.

8. The biocompatible, adjustable flow through system for detection of claim 6 wherein the biocompatible sample input tube is selected from the group consisting of glass, stainless steel or plastic.

9. The biocompatible, adjustable flow through system for detection of claim 8 wherein the biocompatible sample input tube is made from polyether etherketone.

10. The biocompatible, adjustable flow through system for detection of claim 9 wherein the biocompatible sample input tube is supported by a rigid tubing.

11. The biocompatible, adjustable flow through system for detection of claim 6 wherein the biocompatible sample input tube is sealed to the inside of the rigid tubing with a silicone sealant.

12. The biocompatible, adjustable flow through system for detection of claim 6, wherein the upper chamber further comprises O-rings for shock protection and sealing.

13. A flow through detection apparatus for liquid samples comprising:
   a biocompatible sample input system;
   an upper chamber attached to said sample input system by a sealing mechanism;
   a sheath fluid input port attached to said chamber such that it creates an entry point for sheath fluid;
   a rigid elongated tube fixedly attached to said chamber so that the fluid sheath passes within the tube and is directed by the tube;
   a bottom chamber which is attached to the elongated tube and serves as a receptacle for the fluid sheath;
   an illumination apparatus for illuminating the sample with a predetermined wavelength of light as the sample passes through the tube wherein said wavelength of light is selected so as to cause certain of the sample contents to fluoresce;
   detection means which detects the light emitted by the florescence of the sample;
   alignment means which permits a user to adjust the position and attitude of the liquid sample relative to the light source.

14. The flow through detection apparatus for liquid samples of claim 13 wherein said cytometer chamber controls the flow of sample and sheath fluids to be analyzed.

15. The flow through detection apparatus for liquid samples of claim 13 wherein said elongated tube is a square bore capillary constructed so that it is easily removed and replaced.

16. The flow through detection apparatus for liquid samples of claim 13 further comprising a holder fixedly attached to the chamber and constructed to accommodate a removable square bore capillary.

17. The flow through detection apparatus for liquid samples of claim 13 further comprising means for aligning the square bore capillary with the illumination source.

18. The flow through detection apparatus for liquid samples of claim 13 wherein said upper chamber is composed of multiple parts held together by threaded screws and constructed so that when properly fitted together the inner walls form a chamber in which of the sheath fluid may be aligned and its properties adjusted so as to encompass the liquid sample flow.

19. A method for sheath flow cytometry, using a biocompatible, adjustable flow-through cytometer chamber system, comprising the steps of:
   labeling a sample for detection;
   injecting the labeled sample into the cytometer;
   delivering sheath fluid to cytometer;
   slowing of the sheath fluid rate so as to maximize fluorescence detection;
   employing an radiant energy source directed to the sample;
   utilizing an optical system which reduces the scattering of light;
   filtering undesired wavelengths; and
   continuously measuring the fluorescent signals.

20. The method for sheath flow cytometry of claim 19 wherein the sample is labeled with a fluorescent label.

21. The method of sheath flow cytometry of claim 19 wherein the energy source is laser excitation in the red region of the spectrum.

22. The method of sheath flow cytometry of claim 19 wherein the optical system employs a square bore capillary.

23. The method for sheath flow cytometry of claim 19 wherein the laser excitation is a solid state laser.

* * * * *